(12) United States Patent
Woodward et al.

(10) Patent No.: US 9,700,503 B2
(45) Date of Patent: Jul. 11, 2017

(54) COMPOSITION OF ENHANCING HAIR GROWTH

(71) Applicant: Allergan, Inc., Irvine, CA (US)

(72) Inventors: David F. Woodward, Lake Forest, CA (US); Jenny W. Wang, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/561,561

(22) Filed: Dec. 5, 2014

(65) Prior Publication Data
US 2015/0290104 A1 Oct. 15, 2015

Related U.S. Application Data

(62) Division of application No. 13/361,615, filed on Jan. 30, 2012, now Pat. No. 8,932,567.

(60) Provisional application No. 61/437,785, filed on Jan. 31, 2011.

(51) Int. Cl.
| | |
|---|---|
| *A61K 8/00* | (2006.01) |
| *A61K 31/235* | (2006.01) |
| *A61K 8/49* | (2006.01) |
| *A61Q 7/00* | (2006.01) |
| *A61K 8/42* | (2006.01) |
| *A61K 31/215* | (2006.01) |
| *A61K 31/505* | (2006.01) |
| *A61Q 5/00* | (2006.01) |

(52) U.S. Cl.
CPC .............. *A61K 8/4953* (2013.01); *A61K 8/42* (2013.01); *A61Q 7/00* (2013.01); *A61K 31/215* (2013.01); *A61K 31/505* (2013.01); *A61K 2800/592* (2013.01); *A61Q 5/00* (2013.01); Y10S 514/88 (2013.01)

(58) Field of Classification Search
CPC ... A61Q 7/00; A61Q 5/00; A61K 8/42; A61K 8/4953; A61K 31/505; A61K 31/215
USPC .......................... 514/256, 530, 880; 424/70.1
See application file for complete search history.

(56) References Cited

U.S. PATENT DOCUMENTS

| | | | |
|---|---|---|---|
| 4,139,619 A | 2/1979 | Chidsey | |
| 4,968,812 A | 11/1990 | Wang | |
| 5,607,978 A | 3/1997 | Woodward et al. | |
| 7,351,404 B2 | 4/2008 | Woodward | |
| 8,038,988 B2 | 10/2011 | Woodward | |
| 8,101,161 B2 | 1/2012 | Woodward | |
| 8,263,054 B2 | 9/2012 | Woodward | |
| 8,298,518 B2 | 10/2012 | Woodward | |
| 8,932,567 B2 | 1/2015 | Woodward et al. | |
| 2009/0203659 A1 | 8/2009 | Woodward et al. | |

FOREIGN PATENT DOCUMENTS

| | | | |
|---|---|---|---|
| WO | 03-066008 | 8/2003 | |
| WO | 2009-058493 | 5/2009 | |
| WO | WO 2009151828 A1 * | 12/2009 | ............. A61K 8/355 |
| WO | 2011081861 A2 | 7/2011 | |

OTHER PUBLICATIONS

Various: "Has anyone here tried latisse+rogaine?", Heralopecia.com; Mar. 10, 2011 (Mar. 10, 2011), p. 2PP, XP002716936,Retrieved from the Internet: URL:http://www.heralopecia.com/interact/showthread.php/16429-Has-anyone-here-tried-latisse-rogaine?s=860ffec153da033b43593c78f58cde74[retrieved on Nov. 25, 2013] post #6 on p. 2.
Various: "I combine one bottle of Latisse with one bottle of Rogaine",Hairlosstalk.com, Dec. 20, 2009 (Dec. 20, 2009), XP002716937,Retrieved from the Internet: URL:http://www.hairlosstalk.com/interact/showthread.php/45428-I-combine-one-bottle-of-Latisse-with-one-bottle-of-Rogaine?s=4d844a2a03b98ff65a4cbdalb68dfbae; [retrieved on Nov. 25, 2013] posts #1, 4, 12, 13, 15 and 17.
Various: "Latisse & Rogaine",Heralopecia.com, Oct. 13, 2010 (Oct. 13, 2010), XP002716938, Retrieved from the Internet: URL:http://www.heralopecia.com/interact/showthread.php/15792-Latisse-amp-Rogaine, [retrieved on Nov. 25, 2013] post #1.
April Long: "An Innovative Skin-Brightening Line Hits Drugstores", Elle.com, Jul. 23, 2010 (Jul. 23, 2010), p. IOPP, XP002716939, Retrieved from the Internet: URL:http://www.elle.com/beauty/makeup-skin-care/an-innovative-skin-brightening-line•hits-drugstores-455987, [retrieved on Nov. 25, 2013], p. 3, paragraph "You treat hair loss with Latisse and Rogaine. How does it work?"
Patent Cooperation Treaty, International Search Report, PCT/US2012/023148, Jan. 16, 2014.
Ochoa et al., Istilled Bimatoprost Ophthalmic Solution in Patients with Eyelash Alopecia Areata, Journal of American Academy of Dermatology, vol. 61, No. 3, pp. 530-532, Sep. 2009.

* cited by examiner

*Primary Examiner* — Kevin E Weddington
(74) *Attorney, Agent, or Firm* — Lorenz Siddiqi

(57) ABSTRACT

Methods and compositions for stimulating the growth of hair are disclosed wherein said compositions include bimatoprost and minoxidil in a vehicle for topical application to the skin of a mammal, e.g. a human, whereby the combination of bimatoprost and minoxidil produces a faster onset of hair growth in humans or other mammals and wherein said composition brings about a synergistic result of faster onset of hair growth as compared to compositions comprising bimatoprost and minoxidil, alone.

22 Claims, 9 Drawing Sheets

FIGURE 4  Study #10-04 – 0.03% Bimatoprost + 5% Minoxidil

COMPOSITION OF ENHANCING HAIR GROWTH

RELATED APPLICATION

This application is a divisional of U.S. patent application Ser. No. 13/361,615, filed Jan. 30, 2012, which claims the benefit of U.S. Provisional Application Ser. No. 61/437,785, filed Jan. 31, 2011, the disclosures of which are hereby incorporated in their entirety herein by reference.

FIELD OF THE INVENTION

This invention relates to a method for stimulating the growth of mammalian hair comprising the application to mammalian skin of bimatoprost or a pharmacologically acceptable acid addition salt thereof and minoxidil or a pharmacologically acceptable acid addition salt thereof.

BACKGROUND OF THE INVENTION

Dermatologists recognize many different types of hair loss, the most common by far being "alopecia" wherein human males begin losing scalp hair at the temples and on the crown of the head. While this type of hair loss is largely confined to males, hence its common name "male pattern baldness," it is not unknown in women. No known cure has yet been found despite continuing attempts to discover one.

For purposes of the present invention, it is necessary to consider various types of hair, including, terminal hairs and vellus hairs and modified terminal hairs, such as seen in eye lashes and eye brows. Terminal hairs are coarse, pigmented, long hairs in which the bulb of the hair follicle is seated deep in the dermis. Vellus hairs, on the other hand, are fine, thin, non-pigmented short hairs in which the hair bulb is located superficially in the dermis. As alopecia progresses, a transition takes place in the area of approaching baldness wherein the hairs themselves are changing from the terminal to the vellus type.

Another factor that contributes to the end result is a change in the cycle of hair growth. All hair, both human and animal, passes through a life cycle that includes three phases, namely, the anagen phase, the catagen phase and the telogen phase. The anagen phase is the period of active hair growth and, insofar as scalp hair is concerned, this generally lasts from 3-5 years. The catagen phase is a short transitional phase between the anagen and telogen phases which, in the case of scalp hair, lasts only 1-2 weeks. The final phase is the telogen phase which, for all practical purposes, can be denominated a "resting phase" where all growth ceases and the hair eventually is shed preparatory to the follicle commencing to grow a new one. Scalp hair in the telogen phase is also relatively short-lived, some 3-4 months elapsing before the hair is shed and a new one begins to grow.

Under normal hair growth conditions on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

Alopecia is associated with the severe diminution of hair follicles. A bald human subject will average only about 306 follicles per square centimeter, whereas, a non-bald human in the same age group will have an average of 460 follicles per square centimeter. This amounts to a one-third reduction in hair follicles which, when added to the increased proportion of vellus hair follicles and the increased number of hair follicles in the telogen phase, is both significant and noticeable. Approximately 50% of the hairs must be shed to produce visible thinning of scalp hair. It is thus a combination of these factors: transition of hairs from terminal to vellus, increased number of telogen hairs-some of which have been shed, and dimunation and loss of hair follicles that produces "baldness".

While a good deal is known about the results of male pattern baldness, very little is known about its cause. The cause is generally believed to be genetic and hormonal in origin although, the known prior art attempts to control it through hormone adjustment have been, for the most part, unsuccessful.

One known treatment for male pattern alopecia is hair transplantation. Plugs of skin containing hair are transplanted from areas of the scalp where hair is growing to bald areas with reasonable success; however, the procedure is a costly one in addition to being time-consuming and quite painful. Also, psycho-sociological exist and hair transplantation may be viewed as little different from wearing a wig. Furthermore, the solution is inadequate from the standpoint that it becomes a practical, if not an economic, impossibility to replace but a tiny fraction of the hair present in a normal healthy head of hair.

Other non-drug related approaches to the problem include such things as ultra-violet radiation, massage, psychiatric treatment and exercise therapy. None of these, however, has been generally accepted as being effective. Even such things as revascularization surgery and acupuncture have shown little, if any, promise.

By far, the most common approach to the problem of discovering a remedy for hair loss and male pattern alopecia has been one of drug therapy. Many types of drugs ranging from vitamins to hormones have been tried and only recently has there been any indication whatsoever of even moderate success. For instance, it was felt for a long time that since an androgenic hormone was necessary for the development of male pattern baldness, that either systemic or topical application of an antiandrogenic hormone would provide the necessary inhibiting action to keep the baldness from occurring. The theory was promising but the results were uniformly disappointing.

The androgenic hormone testosterone was known, for example, to stimulate hair growth when applied topically to the deltoid area as well as when injected into the beard and pubic regions. Even oral administration was found to result in an increased hair growth in the beard and pubic areas as well as upon the trunk and extremities. While topical application to the arm causes increased hair growth, it is ineffective on the scalp and some thinning may even result. Heavy doses of testosterone have even been known to cause male pattern alopecia.

Certain therapeutic agents have been known to induce hair growth in extensive areas of the trunk, limbs and even occasionally on the face. Such hair is of intermediate status in that it is coarser than vellus but not as coarse as terminal hair. The hair is generally quite short with a length of 3 cm. being about maximum. Once the patient ceases taking the drug, the hair reverts to whatever is normal for the particular site after six months to a year has elapsed. An example of such a drug is diphenylhydantoin which is an anticonvulsant drug widely used to control epileptic seizures. Hypotrichosis is frequently observed in epileptic children some two or three months after starting the drug and first becomes noticeable on the extensor aspects of the limbs and later on the trunk and face. (The same pattern of hypotrichosis is sometimes caused by injury to the head.) As for the hair, it is often shed when the drug is discontinued but may, in some circumstances, remain.

Streptomycin is another drug that has been found to produce hypotrichosis, in much the same way as diphenyl-hydantoin, when administered to children suffering from tuberculous meningitis. About the same effects were observed and the onset and reversal of the hypotrichosis in relation to the period of treatment with the antibiotic leave little question but that it was the causative agent.

Two treatments have been demonstrated as showing some promise in reversing male pattern alopecia. These treatments include the use of a microemulsion cream containing both estradiol and oxandrolone as its active ingredients and the use of organic silicon.

In addition to the foregoing, it has been reported in U.S. Pat. Nos. 4,139,619 and 4,968,812, that the compound minoxidil is useful for the treatment of male pattern baldness. That compound, among others, has proven to have considerable therapeutic value in the treatment of severe hypertension. It is a so-called anti-hypertensive "vasodilator" which, as the name implies, functions to dilate the peripheral vascular system. First introduced as an oral drug to treat high blood pressure, topical solutions and foam products were introduced to prevent or treat hair loss. Dermatologists and others have recognized that prolonged vasodilation of certain areas of the human body other than the scalp sometimes result in increased hair growth even in the absence of any vasodilating therapeutic agent. For instance, increased hair growth around surgical scars is not uncommon. Similarly, arteriovenous fistula have been known to result in increased vascularity accompanied by enhanced hair growth. Externally-induced vasodilation of the skin, such as, for example, by repeated biting of the limbs by the mentally retarded and localized stimulation of the shoulders by water carries has been known to bring on hypotrichosis in the affected areas. Be that as it may, similar techniques such as continued periodic massage of the scalp have been found to be totally ineffective as a means for restoring lost hair growth to the scalp. Scar tissue on the scalp inhibits rather than promotes hair growth.

Bimatoprost, which is sold by Allergan, Inc. of Irvine, Calif., U.S.A. as LATISSE®, is effective in treating hypotrichosis, alopecia and for growing hair.

It is, therefore, a principal object of the present invention to provide a novel and effective combination treatment for the stimulation of hair growth and the treatment of male pattern baldness.

Still another objective is the provision of a treatment for the stimulation of hair growth including eyelashes, eyebrows and scalp and facial hair which, while effective for its intended purpose, is non-toxic and relatively free of unwanted side effects.

An additional object of the invention herein disclosed and claimed is to provide a method for treating hair loss in men or women, including hair loss due to chemotherapy, which can be applied by the patient under medical supervision no more stringent than that demanded for other topically-administered therapeutic agents.

Finally, it is an object of this invention to enhance the growth of eyelashes, eyebrows, scalp hair and facial hair in a human.

SUMMARY OF THE INVENTION

This invention provides pharmaceutical compositions for topical application to enhance hair growth comprising an effective amount cyclopentane N-ethyl heptanamide-5-cis-2-(3α-hydroxy-5-phenyl-1-trans-pentenyl)- 3,5-dihydroxy, [$1_\alpha, 2_\beta, 3_{60}, 5_\alpha$], also known as bimatoprost, and minoxidil. Unpredictably, the combination of bimatoprost and minoxidil synergistically decreases the time of initial hair growth and increases the rate of hair growth, as compared to bimatoprost or minoxidil, alone.

Another aspect of the invention provides methods for stimulating the rate of hair growth and for stimulating the conversion of vellus hair or intermediate hair to growth as terminal hair in a human or non-human by administering to the skin an effective amount of bimatoprost and minoxidil, wherein the combination of bimatoprost and minoxidil obtains the above results in a synergistic manner as compared to bimatoprost and minoxidil, alone.

The method of the present invention can be used to prevent hair loss, to treat hair loss, to treat or thicken thinning hair, loss of eyebrows, loss of eyelashes or facial hair, and can be used to treat all types of alopecia, including hair loss due to chemotherapy and/or exposure to the chemicals or radiation, for treatment of effluviums including telogen effluvium, alopecia areata, scarring alopecia, androgenetic alopecia, self-induced hair loss, congenital hypotrichosis, hair loss due to infection agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, syphilis, lupus and iron deficiency.

Some embodiments of the present invention include:
1. A method for enhancing hair growth in a mammal in need thereof which comprises administering to the mammal a synergistically effective amounts of bimatoprost and minoxidil.
2. The method of paragraph 1 wherein said bimatoprost and said minoxidil are administered to a human.
3. The method of paragraph 1 wherein bimatoprost and minoxidil are administered as a composition comprising from 0.0000001% to 10% bimatoprost and from 0.001% to 10% minoxidil, by weight.
4. The method of paragraph 3 wherein bimatoprost is provided as a pharmaceutically acceptable salt.
5. A method for enhancing hair growth activity of a compound selected from the group consisting of bimatoprost and minoxidil following topical administration of one of said compounds to a mammal in need of treatment to alleviate a condition characterized by inadequate or lack of hair, wherein said method comprises topically or otherwise co-administering said compound to said animal with a synergistically effective amount of the other compound, wherein the amount of said other compound is sufficient to enhance the hair growth activity of said compound.
6. The method as described in paragraph 5 wherein said bimatoprost and said minoxidil is administered to a human.
7. The method of paragraph 5 wherein bimatoprost and minoxidil are administered as a composition comprising from 0.0000001% to 10% bimatoprost and from 0.001% to 10% minoxidil, by weight.
8. The method of paragraph 5 wherein bimatoprost and minoxidil are provided, topically, as a pharmaceutically-acceptable liquid.
9. A method for alleviating a condition characterized by inadequate or lack of hair, in or on a mammal, which comprises topically or otherwise locally administering to said mammal an effective amount of a pharmaceutical composition comprising: (1) a combination of bimatoprost and minoxidil in a synergistically effective amount and (2) a non-toxic, pharmaceutically acceptable carrier therefore suitable for topical or other local application.

10. The method as described in paragraph 9 wherein said bimatoprost and said minoxidil are administered to a human.

11. The method of paragraph 9 wherein bimatoprost and minoxidil are administered as a composition comprising from 0.0000001% to 10% bimatoprost and from 0.001% to 10% minoxidil, by weight.

12. The method of paragraph 9 wherein bimatoprost and minoxidil are provided, topically, as a pharmaceutically-acceptable liquid.

13. A method for the conversion of vellus hair or intermediate hair to growth as terminal hair comprising the application to mammalian skin at the locale of vellus hair of a combination of bimatoprost and minoxidil in a synergistically effective amount.

14. The method as described in paragraph 13 wherein bimatoprost and minoxidil are administered to a human.

15. The method of paragraph 13 wherein bimatoprost and minoxidil are administered as a composition comprising from 0.0000001% to 10% bimatoprost and from 0.001% to 10% minoxidil, by weight.

16. The method of paragraph 13 wherein bimatoprost and minoxidil are provided, topically, as a pharmaceutically-acceptable liquid.

17. A method for stimulating hair follicles to increase hair growth and one or more properties selected from the group consisting of luster, sheen, brilliance, gloss, glow, shine or patina of hair associated with the follicles, comprising the application to mammalian skin at the locale of the follicles of an effective amount of a combination of bimatoprost and minoxidil in a synergistically effective amount.

18. The method of paragraph 17 wherein bimatoprost and minoxidil are administered as a composition comprising from 0.0000001% to 10% bimatoprost and from 0.001% to 10% minoxidil, by weight.

19. The method of paragraph 17 bimatoprost and minoxidil are provided, topically, as a pharmaceutically-acceptable liquid.

20. A composition of bimatoprost and minoxidil in a vehicle for topical application to the skin of a mammal whereby the combination of bimatoprost and minoxidil produces a faster onset of hair growth in humans or other mammals and wherein said composition brings about a synergistic result of faster onset of hair growth as compared to compositions comprising bimatoprost and minoxidil, alone.

21. A method of treating or preventing alopecia caused by chemotherapy which comprises applying to a patient in need thereof an effective amount of bimatoprost and minoxidil in association with a pharmaceutical carrier adapted for topical application to mammalian skin.

22. The method of treating or preventing alopecia caused by chemotherapy, according to paragraph 21, which comprises applying to a patient in need thereof an effective amount of a foam comprising a mixture of bimatoprost and minoxidil, said mixture being adapted for topical application to mammalian skin as a foam produced from a foamable liquid composition, wherein said foamable liquid composition comprises bimatoprost and minoxidil and a surfactant, wherein the surfactant optionally includes a foam stabilizer; and an aqueous-alcohol solvent, wherein said aqueous-alcohol solvent comprises water and an alcohol.

23. A foamable liquid composition, for use in the method of paragraph 1, comprising bimatoprost, minoxidil, a surfactant, wherein the surfactant optionally includes a foam stabilizer; and an aqueous-alcohol solvent, comprising water and an alcohol.

24. The composition of paragraph 23 wherein said foamable liquid composition further comprises an acid and a water soluble solvent, wherein said acid is an inorganic acid, or an organic acid containing eight carbons or less and said water soluble solvent is selected from the group consisting of butylene glycol, glycerin, polyglycerin, ethylene glycol, and propylene glycol.

25. The composition of paragraph 24 wherein said alcohol is selected from the group consisting of methanol, ethanol, propanol and mixtures thereof.

26. The composition of paragraph 25 wherein said acid is lactic acid and said water soluble solvent is propylene glycol.

27. The composition of paragraph 26 wherein said lactic acid is provided at a concentration of from 0.5 to 5 percent, by weight, of the foamable liquid composition and said propylene glycol is provided in an amount of from 1 to 20 percent, by weight, of the foamable liquid composition.

28. The composition of paragraph 27 wherein said alcohol is ethanol and is provided in an amount of from 1 to 50 percent, by weight, of the foamable liquid composition.

29. The composition of paragraph 28 wherein said surfactant is oleth-20 and is provided in an amount of from 0.1 to 5 percent, by weight, of the foamable liquid composition.

30. The composition of paragraph 29 wherein said foam stabilizer is lauryl glucoside and is provided in an amount of from 0.05 to 0.5 percent, by weight, of said foamable liquid composition.

31. A gel comprising bimatoprost and minoxidil in a pharmaceutically-acceptable solvent comprising propylene glycol and alcohol and a cross-linked acrylic polymer thickening agent such as a Carbomer, e.g. Carbomer 934P, wherein the cross-linked acrylic polymer thickening agent is neutralized with a neutralizing agent such as diisopropanolamine 32. A composition in the form of a gel comprising from 0.0000001% to 10% bimatoprost and from 0.001% to 10% minoxidil, by weight, a cross-linked copolymer of acrylic acid as a thickening agent, and a pharmaceutically acceptable solvent.

33. The composition of paragraph 32 which comprises from 0.01% to 0.5% bimatoprost and from 1% to 5% minoxidil, by weight.

34. The composition of paragraph 33 which comprises 0.03% bimatoprost and 5% minoxidil, by weight.

35. The composition of paragraph 32, wherein said pharmaceutically acceptable solvent is selected from the group consisting of ethanol, propanol, butanol, propylene glycol, dipropylene glycol, hexylene glycol, 1,3-butylene glycol, PEG-200, PEG-400, glycerol and mixtures thereof.

36. The composition of paragraph 35, comprising a solvent selected from the group consisting of ethanol, propanol and butanol.

37. The composition of paragraph 35, comprising a solvent selected from the group consisting of ethanol and isopropanol.

38. The composition of paragraph 36, comprising a solvent selected from the group consisting of propylene glycol, 38. dipropylene glycol, hexylene glycol, 1,3-butylene glycol, PEG-200, PEG-400, and glycerol.

39. The composition of paragraph 38, wherein said solvent comprises propylene glycol.

40. A composition of paragraph 36, wherein said solvent comprises a mixture comprising a first solvent selected from the group consisting of ethanol, propanol and butanol and a second solvent selected from the group consisting of propylene glycol, dipropylene glycol, hexylene glycol, 1,3-butylene glycol, PEG-200, PEG-400, and glycerol.

41. The composition of paragraph 40, wherein said solvent comprises a mixture of ethanol and propylene glycol.

42. The composition of paragraph 41, further comprising a neutralizing agent.

43. The composition of paragraph 42, wherein said neutralizing agent is selected from the group consisting of ammonium hydroxide, arginine, 2-amino-2-methyl-1-propanol, dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, aminomethyl propanol, sodium hydroxide, and potassium hydroxide.

44. The composition of paragraph 43, wherein said neutralizing agent is selected from the group consisting of 2-amino-2-methyl-1-propanol, diisopropanolamine, triisopropanolamine, and tetrahydroxypropyl ethylenediamine.

45. The composition of paragraph 44, wherein said neutralizing agent is 2- amino-2-methyl-1-propanol.

46. The composition of paragraph 36, wherein said solvent is present in said composition in an amount of at least about 20%.

47. The composition of paragraph 46 which comprises from about 20% to about 99%, by weight, of said solvent.

48. The composition of paragraph 36, wherein said cross-linked copolymer of acrylic acid comprises an acrylate/$C_{10-30}$ alkyl acrylate cross polymer.

49. The composition of paragraph 48 wherein said solvent is present in said composition in an amount of at least about 20%.

50. A composition in the form of a gel comprising: from about 5% to about 8% of minoxidil and from about 0.01 to about 0.05 bimatoprost; from about 30% to about 80% of a first solvent selected from the group consisting of propylene glycol, dipropylene glycol, hexylene glycol, 1,3-butylene glycol, PEG-200, PEG-400, and glycerol; from about 10% to about 50% a second solvent selected from the group consisting of ethanol, propanol and butanol; from about 0.01% to about 50% of a cross-linked copolymer of acrylic acid; from about 0% to about 3% of a neutralizing agent; and water.

51. A method for enhancing hair growth in a human in need thereof comprising administering to the human a synergistically effective amounts of bimatoprost and minoxidil.

52. A method of paragraph 51 comprising administering to the human a composition comprising from 0.0000001% to 10% w/w bimatoprost and from 0.001% to 10% w/w minoxidil.

53. The method of paragraph 51, wherein said bimatoprost and said minoxidil are administered to a human in a composition comprising 0.1% w/w bimatoprost and about 5% w/w minoxidil.

54. The method of paragraph 51 wherein said bimatoprost and said minoxidil are administered to a human as a composition comprising 0.3% w/w bimatoprost and about 5% minoxidil, by weight.

55. The method as claimed in paragraph 51 wherein said bimatoprost and said minoxidil are administered to a human as a composition comprising 0.3% bimatoprost and about 5% minoxidil, by weight.

56. The method of paragraph 52 wherein the composition is applied to the scalp.

57. A composition comprising bimatoprost and minoxidil in a vehicle for topical application to the skin of a human, whereby the combination of bimatoprost and minoxidil in a single composition produces a faster onset of hair growth in humans compared to the administration of bimatoprost and minoxidil, alone.

58. The composition of claim 57 wherein the composition is adapted for topical application to mammalian skin as a foam, wherein said foamable liquid composition comprises bimatoprost and minoxidil and a surfactant, wherein the surfactant optionally includes a foam stabilizer; an aqueous-alcohol solvent, and wherein said aqueous-alcohol solvent comprises water and an alcohol.

59. The composition of paragraph 57 wherein the composition is adapted for topical application to mammalian skin as a gel, wherein said gel comprises bimatoprost and minoxidil and a surfactant.

60. The composition of paragraph 57 wherein said foamable liquid composition further comprises an acid and a water soluble solvent, wherein said acid is an inorganic acid, or an organic acid containing eight carbons or less and said water soluble solvent is selected from the group consisting of butylene glycol, glycerin, polyglycerin, ethylene glycol, and propylene glycol and said alcohol is selected from the group consisting of methanol, ethanol, propanol and mixtures thereof.

61. The composition of paragraph 60 wherein said acid is lactic acid and said water soluble solvent is propylene glycol.

62. A composition of paragraph 59 wherein the gel is comprising of about 30% to about 80% of a first solvent selected from the group consisting of propylene glycol, dipropylene glycol, hexylene glycol, 1,3-butylene glycol, PEG-200, PEG-400, and glycerol; from about 10% to about 50% a second solvent selected from the group consisting of ethanol, propanol and butanol; from about 0.01% to about 50% of a crosslinked copolymer of acrylic acid; from about 0% to about 3% of a neutralizing agent and water.

63. The composition of paragraph 57 wherein the composition is useful for treating hair loss or to prevent hair loss.

64. The composition of paragraph 63 wherein the composition comprises 0.1% w/w bimatoprost and 5% w/w minoxidil.

65. The composition of paragraph 57 wherein the composition is useful in the treatment of alopecia areata.

66. The composition of paragraph 57 wherein the composition is useful in the treatment of hair loss due to chemotherapy.

67. The composition of paragraph 57 wherein the composition is useful in the treatment of hair loss due to telogen effluvium, alopecia areata, scarring alopecia, androgenetic alopecia, self-induced hair loss, congenital hypotrichosis, hair loss due to infectious agents or disease, hair shaft defects, scleroderma, tinea capitis, alopecia totalis, alopecia universalis, traumatic alopecia, traction alopecia, hair loss due to hormonal changes, hair loss due to hyper and hypothyroidism, alopecia mucinosa, hair loss due to scalp infection, and hair loss due to syphilis, lupus and iron deficiency.

68. The composition of paragraph 57 wherein the composition is applied to one selected from the group consisting of the eyelid margin, eyebrow region or scalp.
69. The composition of paragraph 57 wherein the composition is applied at least once a day.
70. The composition of paragraph 57 wherein the composition comprises 0.3% w/w bimatoprost and 5% w/w minoxidil.

The terms "effective amount," "therapeutically effective amount" or "pharmaceutically effective amount" as used herein refers to that amount of the therapeutic agent sufficient to ameliorate one or more aspects of the disorder. The result can be reduction and/or alleviation of the signs, symptoms, or causes of a disease, or any other desired alteration of a biological system. For example, an "effective amount" for therapeutic uses is the amount of the composition comprising an agent as set forth herein required to provide a clinically significant decrease in an ophthalmic disease. For example, for the given aspect (e.g., length of incidence), a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. An appropriate "effective" amount in any individual case may be determined using techniques, such as a dose escalation study.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "disease" refers to any deviation from the normal health of a mammal and includes a state when disease symptoms are present, as well as conditions in which a deviation (e.g., infection, gene mutation, genetic defect, etc.) has occurred, but symptoms are not yet manifested. According to the present invention, the methods disclosed herein are suitable for use in a patient that is a member of the Vertebrate class, Mammalia, including, without limitation, primates, livestock and domestic pets (e.g., a companion animal). Typically, a patient will be a human patient.

As used herein, "topical application," "topical administration," and "topically administering" are used interchangeably herein and include the administration of a composition to the upper and/or lower eyelid margin, eyebrow region, scalp or face. Topical application or administering may result in the delivery of an active agent to the eye or skin or a localized region of the body.

"Topical formulation" and "topical pharmaceutical composition" are used interchangeably herein and include a formulation that is suitable for topical application to the upper and/or lower eyelid margin, eyebrow region, scalp or face Specific topical formulations can be used for topical, local, regional, or transdermal application of substances.

As used herein, the terms "application," "apply," and "applying" used in reference to a topical composition product or method of using a composition or a product, refer to any manner of administering a topical composition or a product to the eye, the mucosal or dermal area proximal to the eye of a patient which, in medical or cosmetology practice, delivers the composition or the product to patient's eye, the mucosal or dermal area proximal to the eye. Smearing, rubbing, spreading, spraying a topical composition, with or without the aid of suitable devices, on a patient's skin are all included within the scope of the term "application," as used herein. The term "topical" or "topically" in reference to administration or application of a composition or a product refers to epicutaneous administration or application, or administration onto skin. The term "topically active agent" as used herein refers to a compound that is effective in a treatment of a skin condition when administered topically. It is to be understood that topically active agent can have a local or a systemic effect, or both, when administered topically. The term "topical," when used in reference to a composition or a product refers to a composition or a product formulated for topical application.

The abbreviations used herein have their conventional meaning within the chemical, biological or pharmaceutical arts.

The terms "about" and "approximately equal" are used herein to modify a numerical value and indicate a defined range around that value. If "X" were the value, "about X" or "approximately equal to X" would generally indicate a value from 0.90X to 1.10X. Any reference to "about X" minimally indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set.

Thus, "about 7, 9, or 11%" is equivalent to "about 7%, about 9%, or about 11%." "About" may also include variations in the amount that a regulatory body such as the FDA or EMEA would view as bioequivalent to the claimed amount.

As used herein, the phrase "pharmaceutically acceptable salts" refers to salts of the active compound(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, naturally and synthetically derived amino acids. Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others.

"Prodrugs" refer to compounds which are a precursor of a compound and that is converted into its active form, for example, in the body by normal metabolic processes.

These and other aspects of the invention will become apparent from the description of the invention which follows below.

BRIEF DESCRIPTION OF THE DRAWING FIGURES

Figure 8:
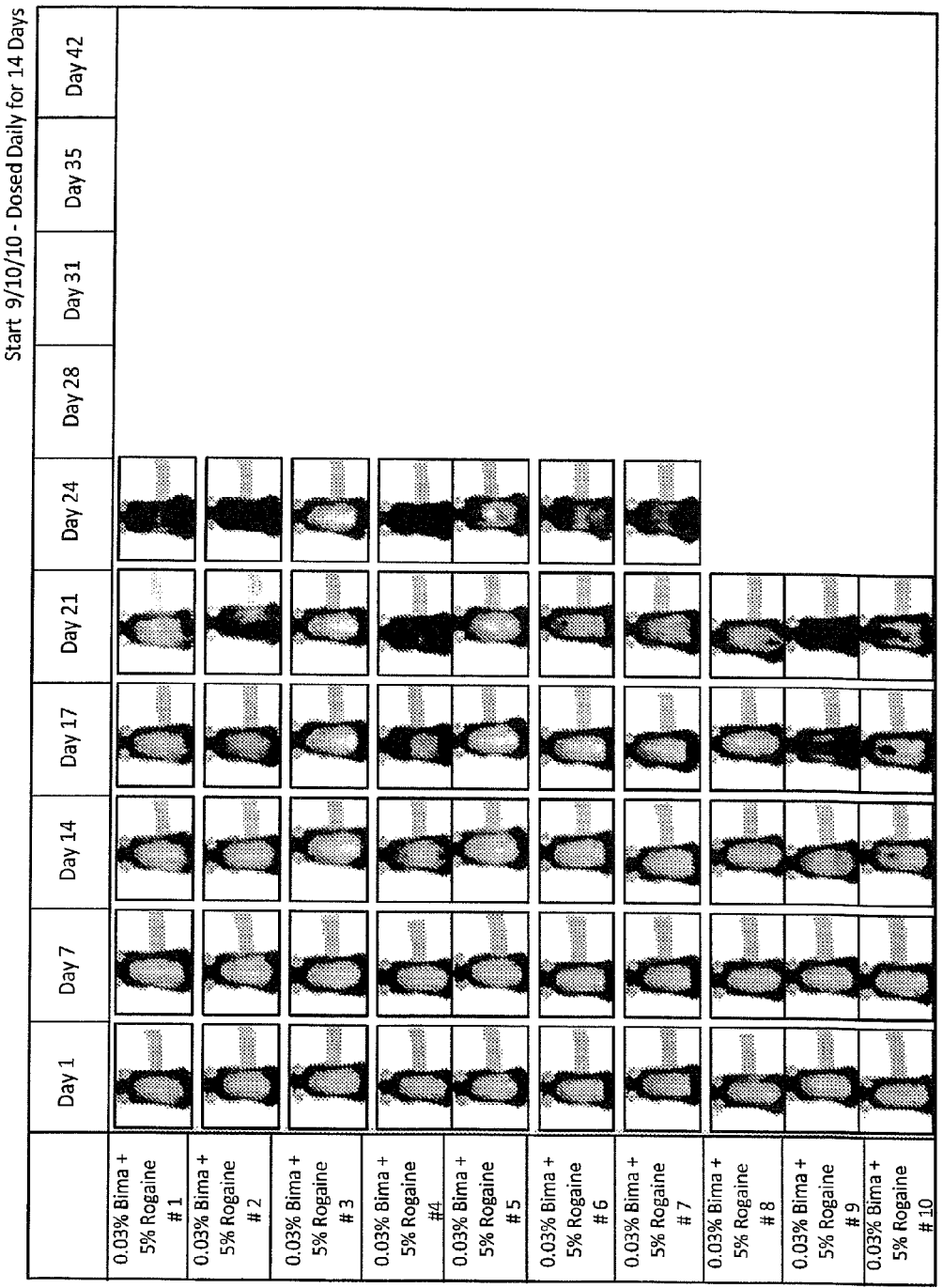
Figure 9:
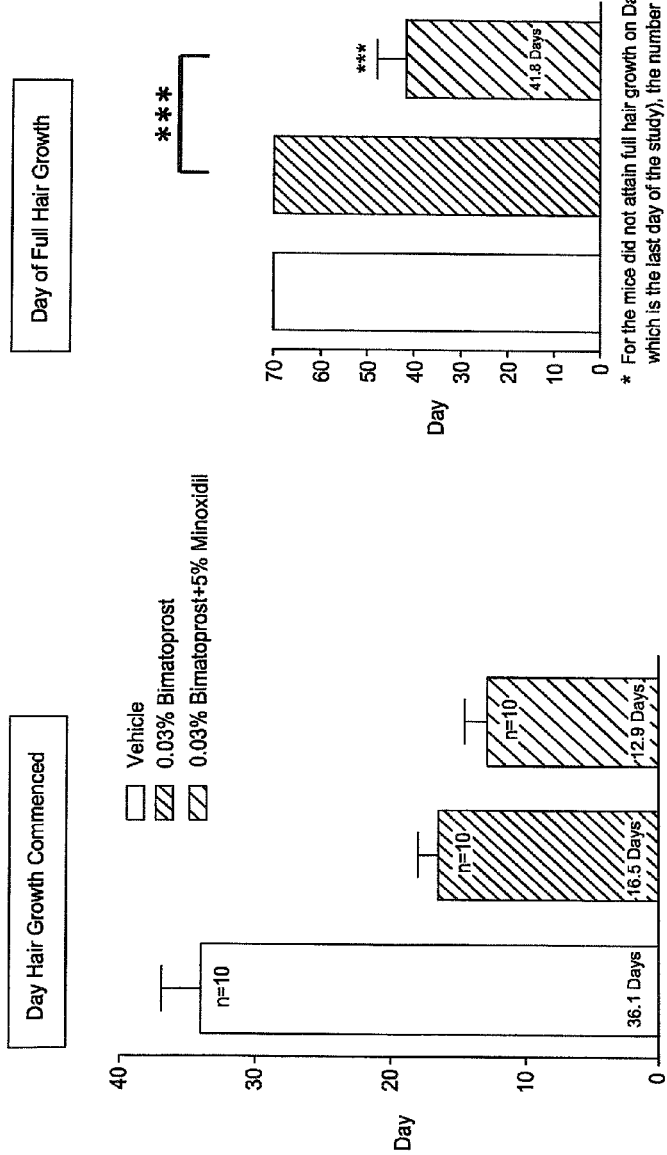

FIG. 8 shows the results of a test of the effect 5% Rogaine (minoxidil), alone, in a mouse model of hair growth; and FIG. 9 shows the results of a 42 day study showing 0.03% bimatoprost in comparison to 0.03% bimatoprost and 5% minoxidil.

DETAILED DESCRIPTION OF THE INVENTION

Alopecia (baldness) a deficiency of either normal or abnormal hair is primarily a cosmetic problem in humans. It is a deficiency of terminal hair, the broad diameter, colored hair that is readily seen. However, in the so-called bald person although there is a noticeable absence of terminal hair, the skin does contain vellus hair which is a fine colorless hair which may require microscopic examination to determine its presence. This vellus hair is a precursor to terminal hair.

Drug synergism occurs when drugs can interact in ways that enhance or magnify one or more effects, or side effects, of those drugs. Negative effects of synergy are a form of contraindication such as when more than one depressant drug is used that affects the central nervous system (CNS), an example being alcohol and Valium. The combination can cause a greater reaction than simply the sum of the individual effects of each drug if they were used separately. In this particular case, the most serious consequence of drug synergy is exaggerated respiratory depression, which can be fatal if left untreated.

Synergism has also been noted in describing how complex systems operate. For example, biological systems may react in a non-linear way to perturbations, so that the outcome may be greater than the sum of the individual component alterations.

In describing the present invention, synergism means that the combination of the two active drugs, utilized in the methods and compositions of the invention achieves a result, e.g. stimulating the growth of hair such as eyelashes, in a mammal, e.g. a human, that is greater than the result achieved when the active drugs are utilized, alone, under the same conditions. Thus, to determine the combinations that are within the scope of the present invention, one may simply compare the result achieved by the combination of the two drugs with the result achieved with each of the individual drugs, alone.

In accordance with the invention as described herein, there is provided a method for enhancing hair growth in a mammal in need thereof which comprises administering to the mammal a synergistically effective amount of bimatoprost and minoxidil. Thus, in accordance with the present invention, synergistically effective amounts of bimatoprost and minoxidil are used to stimulate the conversion of vellus hair to growth as terminal hair as well as increase the rate of growth of terminal hair.

In said method of this invention, the concentration of bimatoprost and minoxidil are administered as a composition comprising from 0.0000001% to 10% bimatoprost and from 0.001% to 10% minoxidil, by weight.

Some concentrations of minoxidil include from about 0.001 to about 5 to about 10% w/w, from about 0.005 to about 5, from about 0.01 to about 5, from about 0.05 to about 5, from about 0.1 to about 5, from about 0.5 to about 5, from about 1 to about 5, from about 1.5 to about 5, from about 2 to about 5, from about 2.5 to about 5, from about 3 to about 5, from about 3.5 to about 5, from about 4 to about 5, from about 4.5, from about 0.001 to about 4.5, from about 0.005 to about 4.5, from about 0.01 to about 4.5, from about 0.05 to about 4.5, from about 0.1 to about 4.5, from about 0.5 to about 4.5, from about 1 to about 4.5, from about 1.5 to about 4.5, from about 2 to about 4.5, from about 2.5 to about 4.5, from about 3 to about 4.5, from about 3.5 to about 4.5, from about 4 to about 4.5, from about 0.001 to about 4, from about 0.005 to about 4, from about 0.01 to about 4, from about 0.05 to about 4, from about 0.1 to about 4, from about 0.5 to about 4, from about 1 to about 4, from about 1.5 to about 4, from about 2 to about 4, from about 2.5 to about 4, from about 3 to about 4, from about 3.5 to about 4, from about 0.001 to about 3.5, from about 0.005 to about 3.5, from about 0.01 to about 3.5, from about 0.05 to about 3.5, from about 0.1 to about 3.5, from about 0.5 to about 3.5, from about 1 to about 3.5, from about 1.5 to about 3.5, from about 2 to about 3.5, from about 2.5 to about 3.5, from about 3 to about 3.5, from about 0.001 to about 3, from about 0.005 to about 3, from about 0.01 to about 3, from about 0.05 to about 3, from about 0.1 to about 3, from about 0.5 to about 3, from about 1 to about 3, from about 1.5 to about 3, from about 2 to about 3, from about 2.5 to about 3, from about 0.001 to about 2.5, from about 0.005 to about 2.5, from about 0.01 to about 2.5, from about 0.05 to about 2.5, from about 0.1 to about 2.5, from about 0.5 to about 2.5, from about 1 to about 2.5, from about 1.5 to about 2.5, from about 2 to about 2.5, from about 0.001 to about 2, from about 0.005 to about 2, from about 0.01 to about 2, from about 0.05 to about 2, from about 0.1 to about 2, from about 0.5 to about 2, from about 1 to about 2, from about 1.5 to about 2, from about 0.001 to about 1.5, from about 0.005 to about 1.5, from about 0.01 to about 1.5, from about 0.05 to about 1.5, from about 0.1 to about 1.5, from about 0.5 to about 1.5, from about 1 to about 1.5, from about 0.001 to about 1, from about 0.005 to about 1, from about 0.01 to about 1, from about 0.05 to about 1, from about 0.1 to about 1, from about 0.5 to about 1, from about 0.001 to about 0.5, from about 0.005 to about 0.5, from about 0.01 to about 0.5, from about 0.05 to about 0.5, from about 0.1 to about 0.5, from about 0.001 to about 0.1, from about 0.005 to about 0.1, from about 0.01 to about 0.1, from about 0.05 to about 0.1, from about 0.001 to about 0.05, from about 0.005 to about 0.05, from about 0.01 to about 0.05, or from about 0.001 to about 0.005% (w/w). In some embodiments, the minoxidil is present at about 0.001, 0.005, 0.01, 0.05, 0.1, 0.5, 1, 1.5, 2, 2.5, 3, 3.5, 4, 4.5, or 5% (w/w).

Minoxidil may also be present in 5.5% w/w to about 10% w/w, from about 6% w/w to about 10% w/w, from about 6.5% w/w to about 10% w/w, from about 7% w/w to about 10% w/w, from about 7.5% w/w to about 10% w/w, from about 8% w/w to about 10% w/w, from about 8.5% w/w to about 10% w/w, from about 9% w/w to about 10% w/w, from about 9.5% w/w to about 10% w/w, from about 5% w/w to about 9.5% w/w, 5.5% w/w to about 9.5% w/w, from about 6% w/w to about 9.5% w/w, from about 6.5% w/w to about 9.5% w/w, from about 7% w/w to about 9.5% w/w, from about 7.5% w/w to about 9.5% w/w, from about 8% w/w to about 9.5% w/w, from about 8.5% w/w to about 9.5% w/w, from about 9% w/w to about 9.5% w/w, from about 5% w/w to about 9% w/w, 5.5% w/w to about 9% w/w, from about 6% w/w to about 9% w/w, from about 6.5% w/w to about 9% w/w, from about 7% w/w to about 9% w/w, from about 7.5% w/w to about 9% w/w, from about 8% w/w to about 9% w/w, from about 8.5% w/w to about 9% w/w, from about 5% w/w to about 8.5% w/w, 5.5% w/w to about 8.5% w/w, from about 6% w/w to about 8.5% w/w, from about 6.5% w/w to about 8.5% w/w, from about 7% w/w to about 8.5% w/w, from about 7.5% w/w to about 8.5% w/w, from about 8% w/w to about 8.5% w/w, from about 5% w/w to about 8% w/w, 5.5% w/w to about 8% w/w, from about 6% w/w to about 8% w/w, from about 6.5% w/w to about 8% w/w, from about 7% w/w to about 8% w/w, from about 7.5% w/w to about 8% w/w, from about 5% w/w to about 7.5% w/w, 5.5% w/w to about 7.5% w/w, from about 6% w/w to about 7.5% w/w, from about 6.5% w/w to about 7.5% w/w, from about 7% w/w to about 7.5% w/w, from about 5% w/w to about 7% w/w, 5.5% w/w to about 7% w/w, from about 6% w/w to about 7% w/w, from about 6.5% w/w to about 7% w/w, from about 5% w/w to about 6.5% w/w, 5.5% w/w to about 6.5% w/w, or from about 6% w/w to about 6.5% w/w. In some embodiments, minoxidil is present at about 5, 5.5, 6, 6.5, 7, 7.5, 8, 8.5, 9, 9.5 or 10% (w/w).

Bimatoprost may be present at 0.1 or 0.3% w/v. Other concentrations that bimatoprost may be present are about 0.005 to about 5, from about 0.01 to about 5, from about 0.05 to about 5, from about 0.1 to about 5, from about 0.5 to about 5, from about 1 to about 5, from about 1.5 to about 5, from about 2 to about 5, from about 2.5 to about 5, from about 3 to about 5, from about 3.5 to about 5, from about 4 to about 5, from about 4.5, from about 0.001 to about 4.5, from about 0.005 to about 4.5, from about 0.01 to about 4.5, from about 0.05 to about 4.5, from about 0.1 to about 4.5, from about 0.5 to about 4.5, from about 1 to about 4.5, from about 1.5 to about 4.5, from about 2 to about 4.5, from about 2.5 to about 4.5, from about 3 to about 4.5, from about 3.5 to about 4.5, from about 4 to about 4.5, from about 0.001 to about 4, from about 0.005 to about 4, from about 0.01 to about 4, from about 0.05 to about 4, from about 0.1 to about 4, from about 0.5 to about 4, from about 1 to about 4, from about 1.5 to about 4, from about 2 to about 4, from about 2.5 to about 4, from about 3 to about 4, from about 3.5 to about 4, from about 0.001 to about 3.5, from about 0.005 to about 3.5, from about 0.01 to about 3.5, from about 0.05 to about 3.5, from about 0.1 to about 3.5, from about 0.5 to about 3.5, from about 1 to about 3.5, from about 1.5 to about 3.5, from about 2 to about 3.5, from about 2.5 to about 3.5, from about 3 to about 3.5, from about 0.001 to about 3, from about 0.005 to about 3, from about 0.01 to about 3, from about 0.05 to about 3, from about 0.1 to about 3, from about 0.5 to about 3, from about 1 to about 3, from about 1.5 to about 3, from about 2 to about 3, from about 2.5 to about 3, from about 0.001 to about 2.5, from about 0.005 to about 2.5, from about 0.01 to about 2.5, from about 0.05 to about 2.5, from about 0.1 to about 2.5, from about 0.5 to about 2.5, from about 1 to about 2.5, from about 1.5 to about 2.5, from about 2 to about 2.5, from about 0.001 to about 2, from about 0.005 to about 2, from about 0.01 to about 2, from about 0.05 to about 2, from about 0.1 to about 2, from about 0.5 to about 2, from about 1 to about 2, from about 1.5 to about 2, from about 0.001 to about 1.5, from about 0.005 to about 1.5, from about 0.01 to about 1.5, from about 0.05 to about 1.5, from about 0.1 to about 1.5, from about 0.5 to about 1.5, from about 1 to about 1.5, from about 0.001 to about 1, from about 0.005 to about 1, from about 0.01 to about 1, from about 0.05 to about 1, from about 0.1 to about 1, from about 0.5 to about 1, from about 0.001 to about 0.5, from about 0.005 to about 0.5, from about 0.01 to about 0.5, from about 0.05 to about 0.5, from about 0.1 to about 0.5, from about 0.001 to about 0.1, from about 0.005 to about 0.1, from about 0.01 to about 0.1, from about 0.05 to about 0.1, from about 0.001 to about 0.05, from about 0.005 to about 0.05, from about 0.01 to about 0.05, or from about 0.001 to about 0.005% (w/w). In some embodiments, bimatoprost is present at about 0.001, 0.005, 0.01, 0.05, 0.1, 0.5, 1, 1.5, 2, 2.5, 3, 3.5, 4, 4.5, or 5% (w/w).

In one aspect of the invention, there is provided a method for enhancing hair growth activity of a compound selected from the group consisting of bimatoprost and minoxidil following topical administration of one of said compounds to a warm-blooded animal in need of treatment to alleviate a condition characterized by inadequate or lack of hair, wherein said method comprises topically or otherwise co-administering said compound to said animal with a synergistically effective amount of the other compound, wherein the amount of said other compound is sufficient to enhance the hair growth activity of said compound.

Preferably, in this aspect of the method of this invention the concentration bimatoprost and minoxidil are administered as a composition comprising from 0.0000001% to 10% bimatoprost and from 0.001% to 10% minoxidil, by weight.

In a further aspect of the invention, there is provided a method for alleviating a condition characterized by inadequate or lack of hair, in or on a warm-blooded animal, which comprises topically or otherwise locally administering to said animal an effective amount of a pharmaceutical composition comprising: (1) a combination of bimatoprost and minoxidil in a synergistically effective amount and (2) a non-toxic, pharmaceutically acceptable carrier therefore suitable for topical or other local application.

In a still further aspect of the invention there is provided a method for the conversion of vellus hair or intermediate hair to growth as terminal hair comprising the application to mammalian skin at the locale of vellus hair of a combination of bimatoprost and minoxidil in a synergistically effective amount.

Finally, the instant invention provides a method for stimulating hair follicles to increase hair growth and one or more properties selected from the group consisting of luster, sheen, brilliance, gloss, glow, shine or patina of hair associated with the follicles, comprising the application to mammalian skin at the locale of the follicles of an effective amount of a combination of bimatoprost and minoxidil in a synergistically effective amount.

In addition to the disclosed methods of this invention there is provided a composition of bimatoprost and minoxidil in a vehicle for topical application to the skin of a mammal whereby the combination of bimatoprost and minoxidil produces a faster onset of hair growth in humans or animals and wherein said composition brings about a synergistic result of faster onset of hair growth as compared to compositions comprising bimatoprost and minoxidil, alone.

It has now been surprisingly found that the use of bimatoprost in combination with minoxidil improves the results achieved with bimatoprost, alone. Indeed, this improvement is synergistic in nature, in that the results in improving or enhancing the growth of hair are greater than those obtained with minoxidil, alone, as well.

One of the compounds used in the practice of the present invention is cyclopentane N-ethyl heptanamide-5-cis-2-(3α-hydroxy-5-phenyl-1-trans-pentenyl)-3,5-dihydroxy, [1$_\alpha$,2$_\beta$, 3$_\alpha$,5$_\alpha$], also known as bimatoprost and sold under the name of Lumigan® by Allergan, Inc., California, USA. This compound has the following structure:

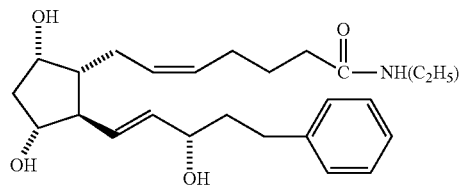

The synthesis of the compound, described above, has been disclosed in U.S. Pat. No. 5,607,978 which is hereby incorporated by reference in its entirety. This patent also shows that it does not behave as a prostaglandin in art-recognized assays for prostaglandin activity. The invention thus relates to the use of the above compound, or salts thereof for the stimulation of hair growth. As used herein, hair growth includes hair associated with the scalp, eyebrows, eyelids, beard, and other areas of the skin of animals. Bimatoprost also includes bimatoprost prodrugs, salts and isomers.

The other compound, minoxidil is a vasodilator medication known for its ability to slow or stop hair loss and promote hair regrowth. It is available over the counter for treatment of androgenic alopecia, among other baldness treatments, but measurable changes disappear within months after discontinuation of treatment. Minoxidil has the structure

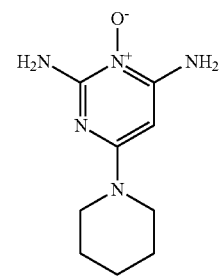 [SMILES: Nc1cc(N2CCCCC2)nc(N)[n+]1[O-]]

and may include physiologically acceptable salts, prodrugs and isomers.

In accordance with one aspect of the invention, the drugs, i.e. bimatoprost and minoxidil, are mixed with a dermatologically compatible vehicle or carrier. The vehicle which may be employed for preparing compositions of this invention may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to dermatological compositions for topical treatment for the stimulation of hair growth, which comprise an effective hair growth stimulating amount of bimatoprost and minoxidil and a dermatologically compatible carrier. Effective amounts of the active compounds may be determined by one of ordinary skill in the art but will vary depending on the frequency of application and desired result, and bimatoprost will range from about 0.0000001 to about 10%, by weight, of the dermatological composition, preferably from about 0.001 to about 10%, by weight, of total dermatological composition, more preferably from about 0.03 to about 5%, by weight, of the composition and minoxidil will range from about 0.001 to about 10%, by weight, of the dermatological composition, preferably from about 0.01 to about 10%, by weight, of the composition.

The following specific combinations of bimatoprost and minoxidil in a dermatologically compatible carrier are contemplated as being effective to achieve the object of this invention, i.e. enhancing hair growth in a mammal in need thereof by administering to the mammal an effective amount of bimatoprost and minoxidil: Certain of these combinations are synergistic. Other specific combinations within the scope of the concentrations, given below, i.e. 0.1 to 10 percent minoxidil and 0.01 and 0.5 bimatoprost are also contemplated as useful in the method of the present invention.

TABLE I

| Bimatoprost Weight percent w/w | Minoxidil Weight percent w/w |
| --- | --- |
| 0.01 | any one of 0.1, 1.0, 2.0, 3.0, 4.0, 5.0, 6.0, 7.0, 8.0, 9.0 and 10.0; |
| 0.02 | and any one of 0.1, 1.0, 2.0, 3.0, 4.0, 5.0, 6.0, 7.0, 8.0, 9.0 and 10.0; |
| 0.03 | and any one of 0.1, 1.0, 2.0, 3.0, 4.0, 5.0, 6.0, 7.0, 8.0, 9.0 and 10.0; |
| 0.04 | and any one of 0.1, 1.0, 2.0, 3.0, 4.0, 5.0, 6.0, 7.0, 8.0, 9.0 and 10.0; |
| 0.05 | and any one of 0.1, 1.0, 2.0, 3.0, 4.0, 5.0, 6.0, 7.0, 8.0, 9.0 and 10.0; |
| 0.1 | and any one of 0.1, 1.0, 2.0, 3.0, 4.0, 5.0, 6.0, 7.0, 8.0, 9.0 and 10.0; |
| 0.2 | and any one of 0.1, 1.0, 2.0, 3.0, 4.0, 5.0, 6.0, 7.0, 8.0, 9.0 and 10.0; |
| 0.3 | and any one of 0.1, 1.0, 2.0, 3.0, 4.0, 5.0, 6.0, 7.0, 8.0, 9.0 and 10.0; |
| 0.5 | and any one of 0.1, 1.0, 2.0, 3.0, 4.0, 5.0, 6.0, 7.0, 8.0, 9.0 and 10.0 and |
| 1.0 | and any one of 0.1, 1.0, 2.0, 3.0, 4.0, 5.0, 6.0, 7.0, 8.0, 9.0 and 10.0. |

In particular, the following specific combinations of bimatoprost and minoxidil in a dermatologically compatible carrier are contemplated as being effective to achieve the object of this invention, i.e. enhancing hair growth in a mammal in need thereof by administering to the mammal an effective amount of bimatoprost and minoxidil:

TABLE 2

| Bimatoprost Weight percent w/w | Minoxidil Weight percent w/w |
| --- | --- |
| 0.01 | 0.1 |
| 0.01 | 1.0 |
| 0.02 | 2.0 |
| 0.03 | 3.0 |
| 0.04 | 4.0 |
| 0.05 | 5.0 |
| 0.06 | 6.0 |
| 0.07 | 7.0 |
| 0.1 | 8.0 |
| 0.3 | 9.0 |
| 0.5 | 10.0 |

The present invention finds application in all mammalian species, including both humans and animals. In humans, the compounds of the subject invention can be applied for example, to the scalp, face, beard, head, pubic area, upper lip, eyebrows, and eyelids. In animals raised for their pelts, e.g., mink, the drug can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated by this invention include pharmaceutical compositions suited for topical and local action.

The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin surface to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the drug is applied repeatedly for a sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably at least six months.

For topical use on the eyelids or eyebrows, the drug can be formulated in aqueous solutions, creams, ointments or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid etc. as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels. Depending on the actual formulation, various amounts of the drug and different dose regimens may be employed. Typically, the daily amount of each of bimatoprost and minoxidil for treatment of the eyelid may be from about 0.1 ng to about 100 mg per eyelid.

For topical use on the skin and the scalp, the drug can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betaine, chlorhexidine, benzalkonium chloride, and the like. Various matrices for slow release delivery may also be used. To achieve the daily amount of medication depending on the formulation, the compound may be administered once or several times daily with or without antioxidants.

The invention is further illustrated by the following non-limiting examples.

EXAMPLE 1

In Vivo Treatment

A study is initiated to systematically evaluate the appearance of lashes and hair around the eyes of patients by administering a topical composition comprising 0.03% bimatoprost and 5% minoxidil, by weight, in the area of the eyelid of only one eye. The study involves 10 subjects, 5 male, 5 female, average age 70 years, (ranging from 50-94 years). Each subject is treated daily by the topical application of one drop of bimatoprost at a dosage of 1.5 µg/ml/eye/day to the region of one eye by instilling the drop onto the surface of the eyelid. The region of the fellow control eye is not treated and served as a control.

Observations are made under high magnification at the slit lamp biomicroscope. Documentation of differences between the control and treatment areas is accomplished using a camera specially adapted for use with the slit lamp biomicroscope.

The results of the observations will be as follows:

Length of lashes: Increased length of eyelashes is regularly observed on the side treated with bimatoprost. The difference in length varies from approximately 10% to as much as 30%.

Number of lashes: Increased numbers of lashes are observed in the treated eye of each patient. In areas where there are a large number of lashes in the control eye, the increased number of lashes in the treated eye gave the lashes on the treated side a more thickly matted overall appearance.

Auxiliary lash-like hair growth: Several patients have an apparent increase in lash-like hair in transitional areas adjacent to areas of normal lash distribution. These prominent robust appear lash-like hairs appeared to be of comparable length to the actual lashes. These long, thick lash-like hairs were present in the central portion of the lids of several patients in a linear arrangement just above the lash line. Hairs are present at similar locations in the control eyes but are by contrast thinner or finer in appearance, have less luster and pigment and are more flat against the skin of the lid typical of vellus or intermediate hairs. In several patients, lash-like terminal hairs grow luxuriantly in the medial canthal area in the treated eye. In the corresponding control eye, vellus hairs are seen at the same location. Lash-like hairs are also present in the lateral canthal area of the treated eye but not the control eye in several subjects. Large lashes are not normally present at the lateral canthus and the area is generally free of all but a few occasional very fine lashes or vellus hairs.

Increased growth of vellus hair on lids: Fine microscopic vellus hair is present on the skin of the lids and is easily seen with the slit lamp biomicroscope. This vellus hair is typically denser adjacent to and below the lateral portion of the lower lids. While remaining microscopic, vellus hairs are increased in number appear more robust and are much longer and thicker in treated than in control eyes in the areas below and lateral to the lower lid.

Perpendicular angulation of hairs: In areas where there are lash-like hairs above the lash line and in the medial and lateral canthal areas, the hairs are much longer, thicker and heavier. They also leave the surface of the skin at a more acute angle, as though they are stiffer or held in a more erect position by more robust follicles. This greater incline, pitch, rise or perpendicular angulation from the skin surface gives the appearance of greater density of the hairs.

The foregoing observations will clearly establish that above composition can be used to increase the growth of hair in man. This conclusion is based on the regular and consistent finding of manifestations of increased hair growth in treated vs. control areas in human subjects. The conclusion that the composition of this invention is capable of inducing increased robust growth of hair is based not on a single parameter, i.e., length, but is based on multiple lines of evidence as described in the results. Detailed examination and description of multiple parameters of differences in hair is greatly facilitated by the ability to examine the hairs at high magnification under stable conditions of fixed focal length and subject position utilizing the capabilities of the slitlamp biomicroscope.

EXAMPLE 2

Topical Cream

A topical cream is prepared as follows: Tegacid and spermaceti are melted together at a temperature of 70-80° C. Methylparaben is dissolved in about 500 gm of water and propylene glycol, polysorbate 80, and bimatoprost and minoxidil are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

EXAMPLE 3

A topical cream is prepared as follows: Tegacid and spermaceti are melted together at a temperature of 70-80° C. Methylparaben is dissolved in water and propylene glycol, polysorbate 80, and bimatoprost and minoxidil are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

The composition is applied to bald human scalp once daily to stimulate the growth of hair.

EXAMPLE 4

An ointment containing bimatoprost and minoxidil is prepared as follows:

White petrolatum and wool fat are melted, strained and liquid petrolatum is added thereto. The bimatoprost, minoxidil, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

The foregoing ointment can be applied topically to mammalian skin for increased rate of hair growth, and can be prepared by omitting the zinc oxide and calamine.

EXAMPLE 5

A dermatological ophthalmic ointment containing bimatoprost and minoxidil is prepared by adding the active compounds to light liquid petrolatum. White petrolatum is melted together with wool fat, strained, and the temperature adjusted to 45-50° C. The liquid petrolatum slurry is added and the ointment stirred until congealed. Suitably the ointment is packaged in 30 gm tubes.

The foregoing ointment can be applied to the eyelid to enhance the growth of eyelashes. Similarly the composition can be applied to the brow for eyebrow growth.

EXAMPLE 6

An aqueous solution containing bimatoprost and minoxidil is prepared as follows. bimatoprost and minoxidil are dissolved in water and the resulting solution is sterilized by filtration. The solution is aseptically filled into sterile containers.

The composition so prepared can be used in the topical treatment of baldness by application to the scalp daily.

EXAMPLE 7

Bimatoprost and minoxidil are dissolved in a vehicle of N-methyl pyrrolidone and propylene glycol. The composition can be used for application to dogs or cats having hair loss due to mange or alopecia of other causes.

EXAMPLE 8

Aerosol

An aerosol containing approximately 0.03% by weight bimatoprost and 5%, by weight minoxidil is prepared by dissolving the bimatoprost and minoxidil in absolute alcohol. The resulting solution filtered to remove particles and lint. This solution is chilled to about minus 30° C. To the solution is added a chilled mixture of dichlorodifluoromethane and dichlorotetrafluoroethane.

Thirteen ml plastic-coated amber bottles are cold filled with 11.5 gm each of the resulting solution and capped.

The composition can be sprayed on the scalp daily to stimulate the growth of hair.

EXAMPLE 9

A powder of the compound bimatoprost and minoxidil is prepared by mixing in dry form with talcum powder at a weight/weight ratio of 1:10. The powdered mixture is dusted on the fur of minks or other commercially valuable fur bearing animals and show animals for increased rate of hair growth.

EXAMPLE 10

Figure 1:
FIG. 1 shows the results of a test of the effect of the vehicle in a mouse model of hair growth.
Figure 2:
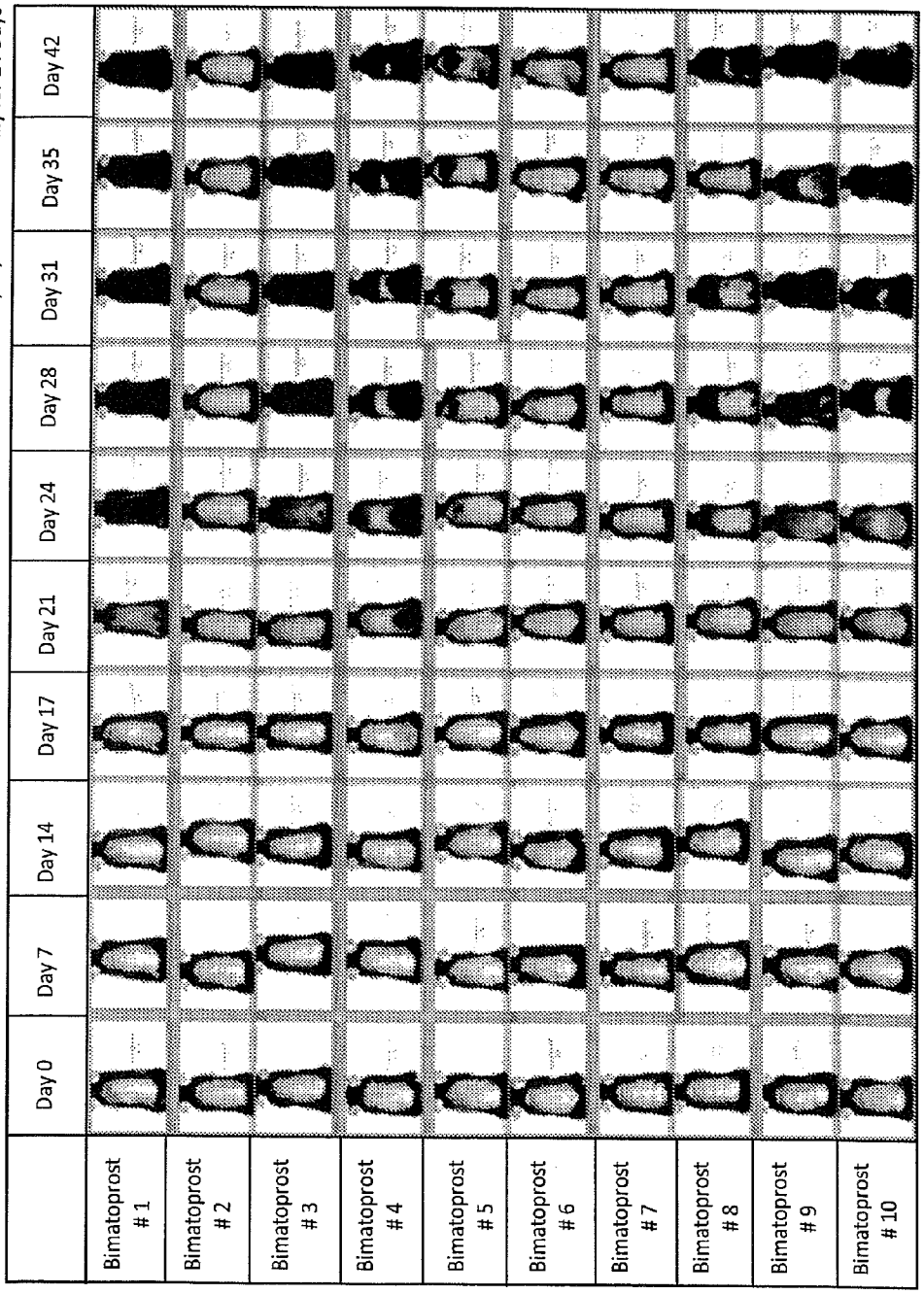
FIG. 2 shows the results of a test of the effect of 0.03% Bimatoprost, alone, in a mouse model of hair growth.
Figure 3:
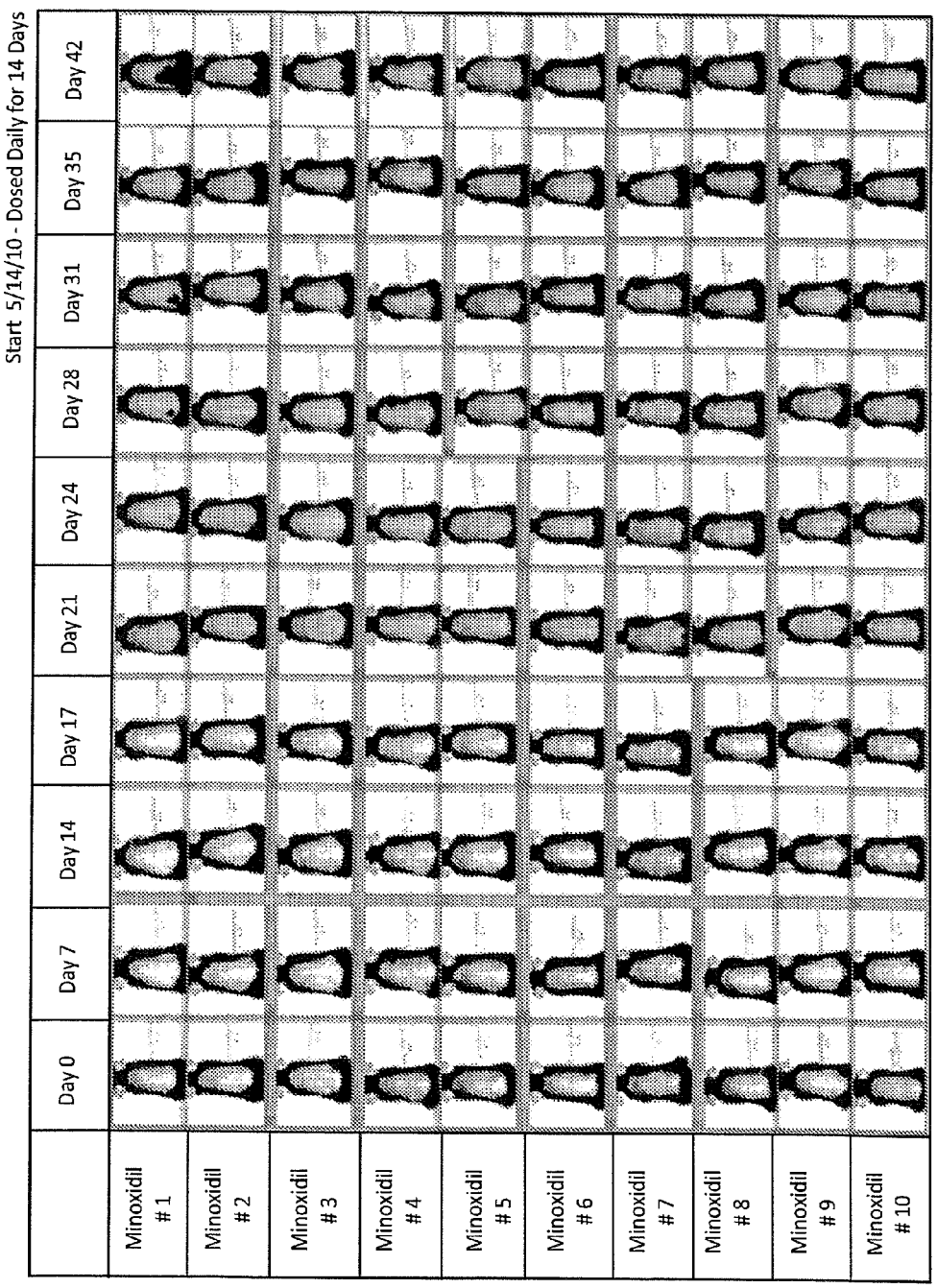
FIG. 3 shows the results of a test of the effect 5% Rogaine (minoxidil), alone, in a mouse model of hair growth.
Figure 4:
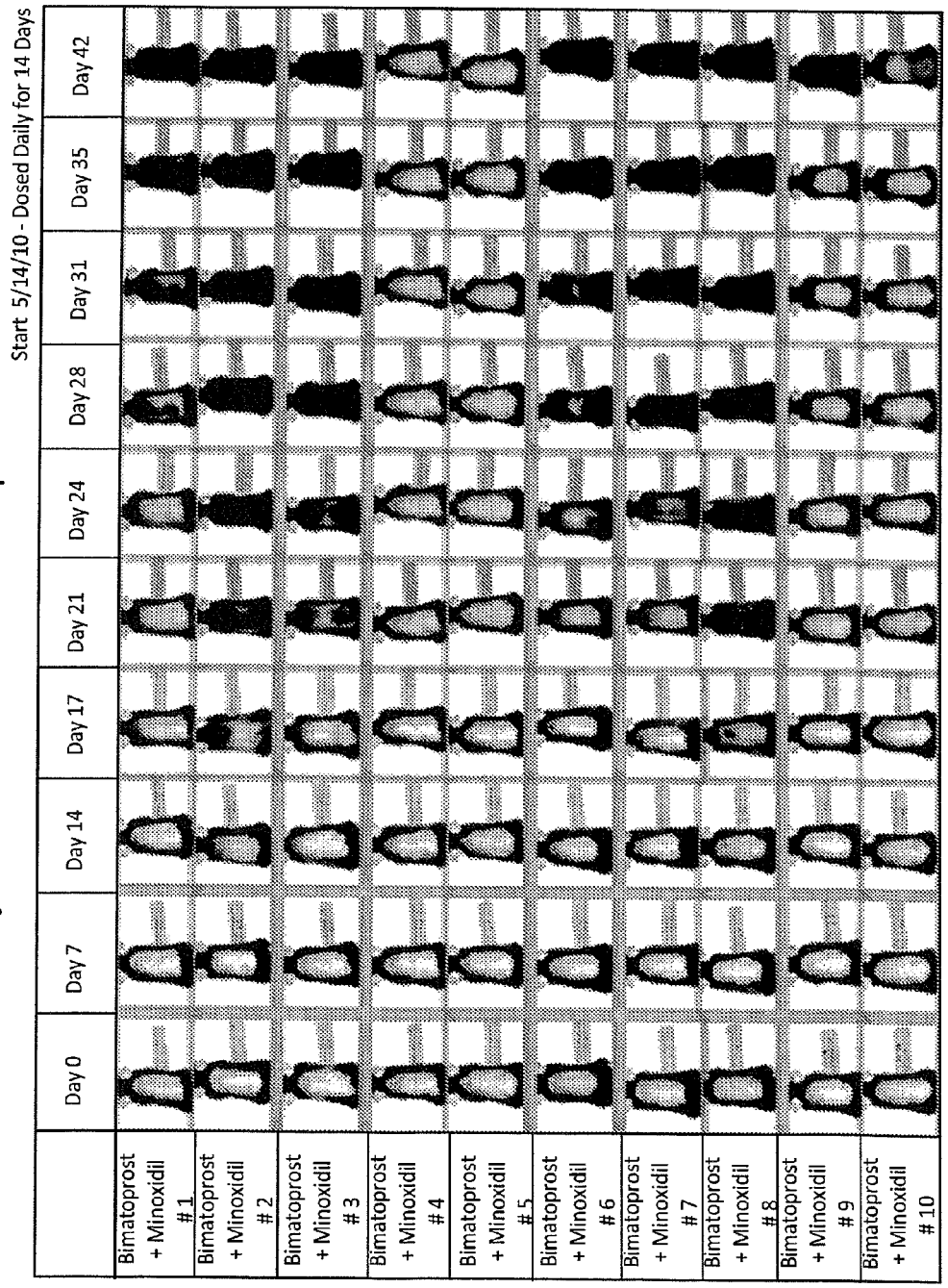
FIG. 4 shows the results of a test of the effect of a synergistic composition, i.e. 0.03% Bimatoprost and 5% Rogaine (minoxidil) in a mouse model of hair growth.
Figure 5:
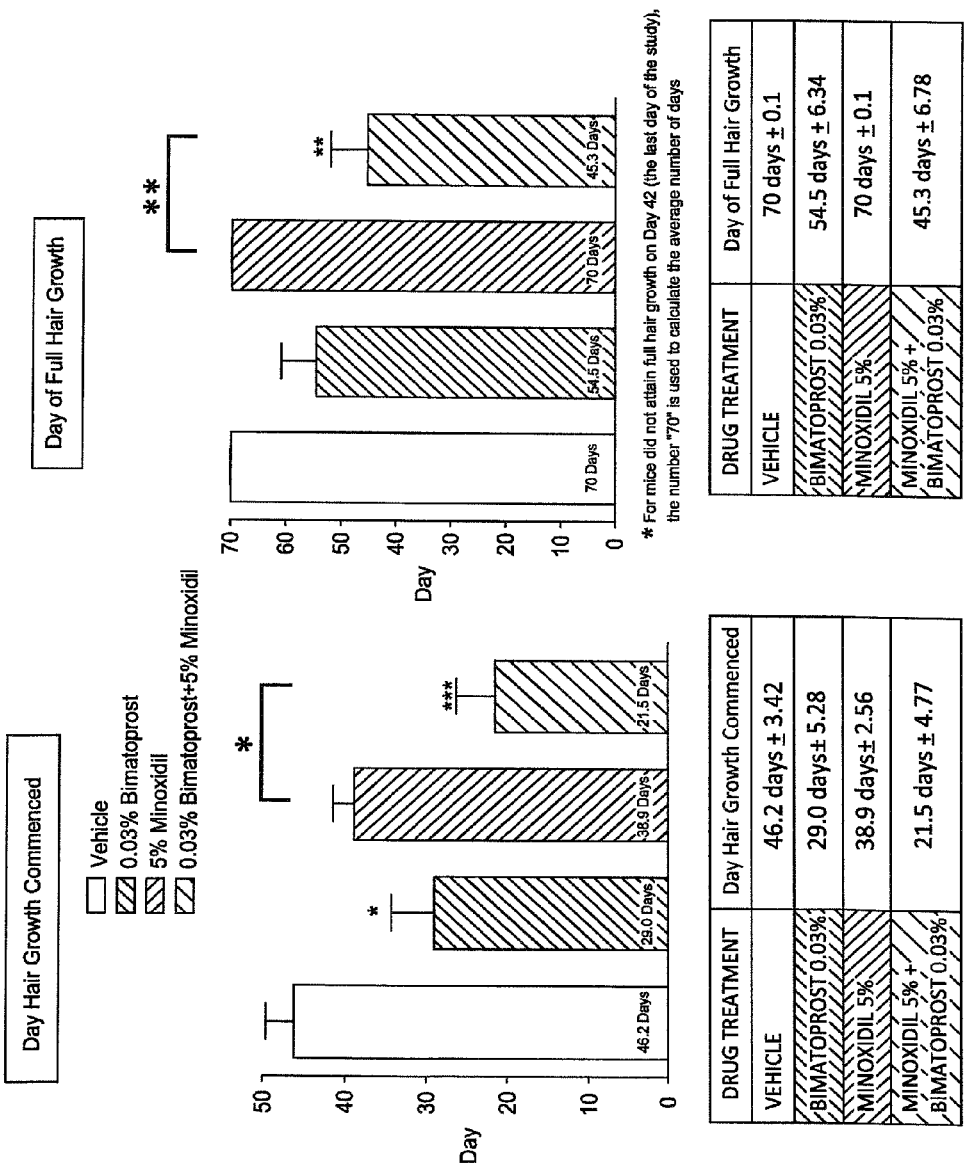
FIG. 5 is a summary of the results of the tests of FIGS. 1 through 4.

In-vivo Animal Studies:

A comparison of topical compositions comprising bimatoprost or minoxidil, alone, and the combination of bimatoprost and minoxidil, in a single composition, with the vehicle, for onset of hair growth and full hair growth, in a mouse model for hair growth, gave the results summarized in Table 1, below, and FIG. 5. The individual test subjects, i.e. the mice, are shown in FIGS. 1 through 4, with FIG. 1 being the Vehicle, FIG. 2 being 0.03% Bimatoprost alone, FIG. 3 being 5% Rogaine (minoxidil) alone, and FIG. 4 being the synergistic composition, i.e. 0.03% Bimatoprost+ 5% Rogaine (minoxidil).) As shown, in this study, all of the compositions having bimatoprost and minoxidil, alone, or in combination, show faster onset of hair growth, but the combination of bimatoprost and minoxidil showed faster onset of hair growth than bimatoprost and minoxidil, alone. In this study, it is shown that bimatoprost and minoxidil, alone, did not obtain the result of full hair growth faster than the vehicle, however, the combination of bimatoprost and minoxidil achieved full hair growth much faster than vehicle and bimatoprost, alone.

TABLE 1

Summary of Study 10-04 (Test One)

DRUG TREATMENT

| | Day Hair Growth Commenced |
|---|---|
| VEHICLE | 46.2 days ± 3.42 |
| BIMATOPROST 0.03% | 29.0 days ± 5.28 |
| MINOXIDIL 5% | 38.9 days ± 2.56 |
| MINOXIDIL 5% + BIMATOPROST 0.03% | 21.5 days ± 4.77 |
| | Day of Full Hair Growth |
| VEHICLE | 70 days ± 0.1 |
| BIMATOPROST 0.03% | 54.5 days ± 6.34 |
| MINOXIDIL 5% | 70 days ± 0.1 |
| MINOXIDIL 5% + BIMATOPROST 0.03% | 45.3 days ± 6.78 |

Figure 6:
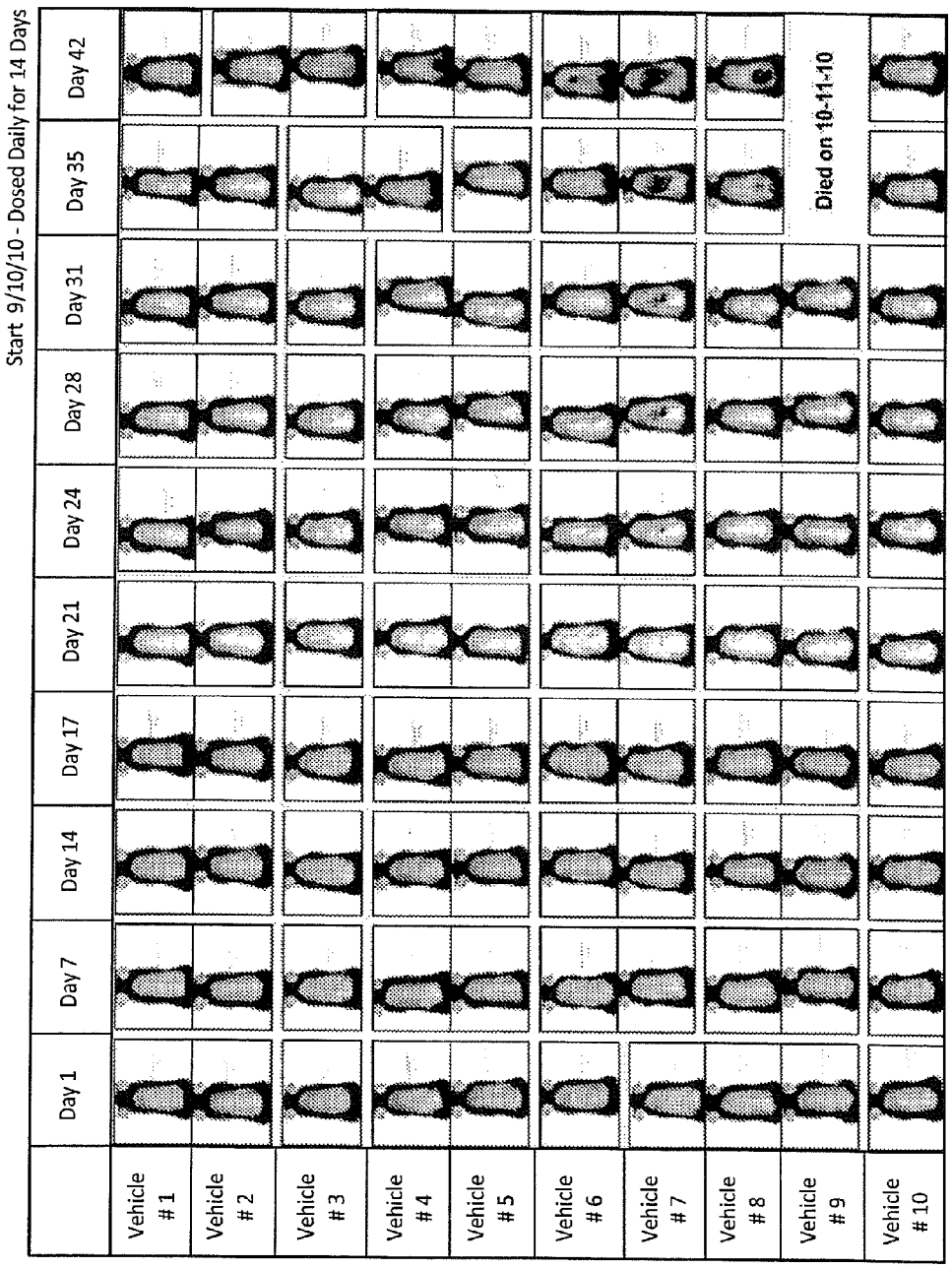
FIG. 6 shows the results of a test of the effect of the vehicle in a mouse model of hair growth.
Figure 7:
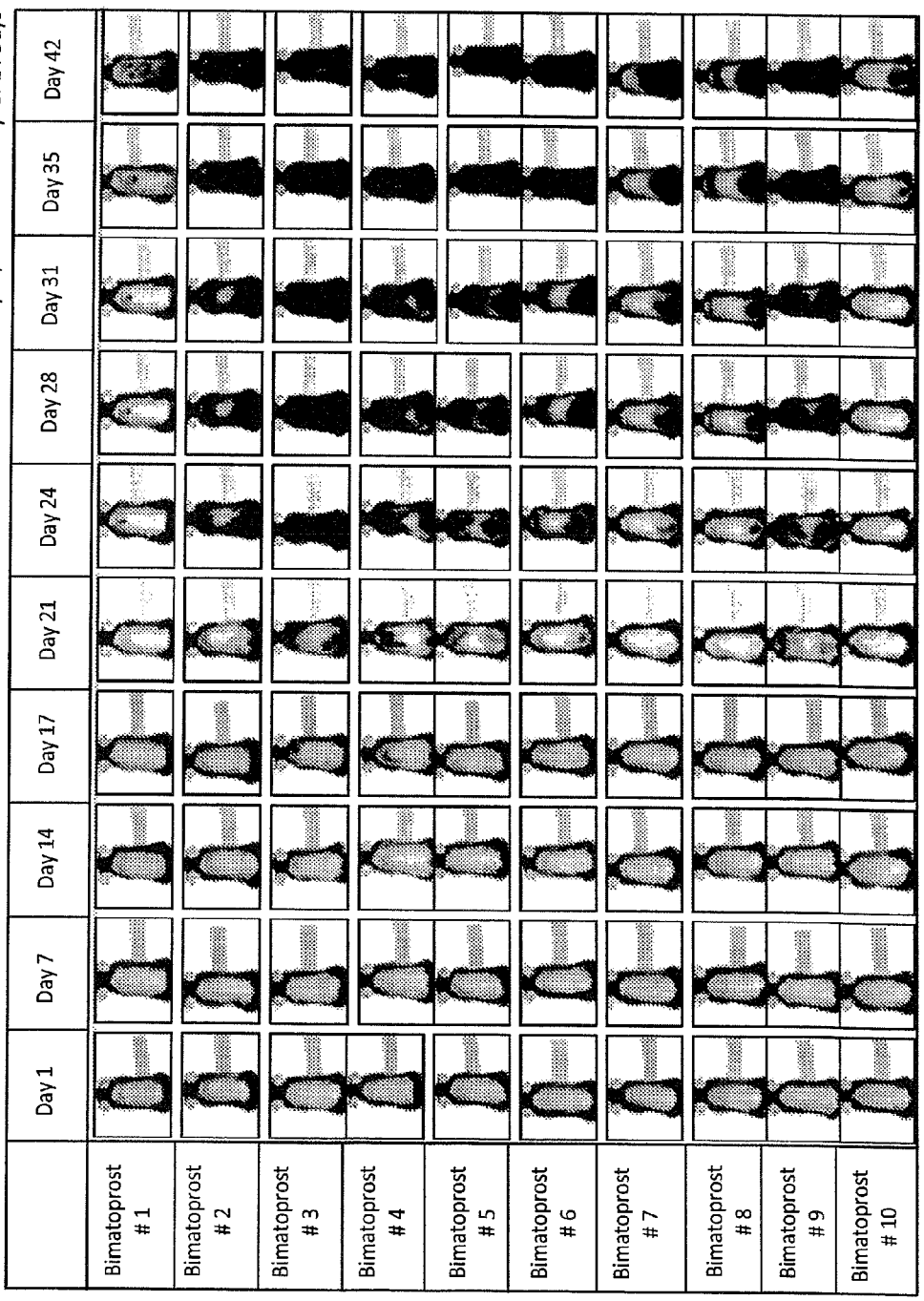
FIG. 7 shows the results of a test of the effect of 0.03% Bimatoprost, alone, in a mouse model of hair growth.

FIGS. 6 through 8 show the results of a separate testing (Test Two) of synergistic composition of the invention in the same mouse model of hair growth, with FIG. 6 being the Vehicle, FIG. 7 being 0.03% Bimatoprost, alone, and FIG. 8 being the synergistic composition, i.e. 0.03% Bimatoprost and 5% Rogaine (minoxidil). These results are summarized in Table 2, below, and FIG. 9.

TABLE 2

Summary of Study 10-06 (Test Two)

DRUG TREATMENT

| | Day Hair Growth Commenced |
|---|---|
| VEHICLE | 36.1 days ± 3.65 |
| BIMATOPROST 0.03% | 16.5 days ± 1.52 |
| MINOXIDIL 5% + BIMATOPROST 0.03% | 12.9 days ± 1.63 |
| | Day of Full Hair Growth |
| VEHICLE | 70 days ± 0.1 |
| BIMATOPROST 0.03% | 70 days ± 0.1 |
| MINOXIDIL 5% + BIMATOPROST 0.03% | 41.8 days ± 6.2 |

Again, as shown in this study, all of the compositions having bimatoprost, alone, or in combination, show faster onset of hair growth, but the combination of bimatoprost and minoxidil showed faster onset of hair growth than bimatoprost, alone. In this study, it is shown that bimatoprost, alone, did not obtain the result of full hair growth faster than the vehicle, however, the combination of bimatoprost and minoxidil achieved full hair growth much faster than vehicle.

EXAMPLE 11

A foamable liquid composition containing approximately 0.03% by weight bimatoprost and 5%, by weight minoxidil is prepared by dissolving the bimatoprost and minoxidil in an alcohol-containing solvent. Said foamable liquid composition further includes a solvent system, a surfactant and a foam stabilizer. The solvent system, includes water, an alcohol and optionally, an acid and a water soluble solvent. This composition is prepared by methods known in the art.

A method of delivering a foam product according to the present invention comprises the following steps:

providing a foamable liquid composition comprising 5 percent, by weight, minoxidil and 0.03 percent, by weight, bimatoprost or a pharmaceutically acceptable salt of either or both of minoxidil or bimatoprost, in an amount or amounts sufficient to provide: 5 percent, by weight, minoxidil, and 0.03 percent, by weight, bimatoprost in a container adapted for dispensing the foamable liquid composition as a foam and dispensing the foamable liquid composition as a foam from said container onto the skin of a patient.

Alternatively, minoxidil may be used in an amount of from 0.5 to 10 percent and preferably in an amount of from 2 to 5 percent, by weight, relative to the total weight of the foamable liquid composition.

Bimatoprost may be used in an amount of from 0.01 to 3 percent and more preferably in an amount of from 0.03 to 1 percent, by weight, relative to the total weight of the liquid composition.

The solvent system is an aqueous-alcoholic medium, which enables solubilization of minoxidil and bimatoprost. In one example, the foamable liquid composition includes from 30 to 80 percent water, by weight. Preferably the foamable liquid composition comprises from 30 to 60 percent water, by weight.

Preferably, the foamable liquid composition further includes an acid at a concentration of from 0.5 to 5 percent, by weight, of the foamable liquid composition. The acid may be selected from the group consisting of an inorganic acid, an organic acid with chain length of eight carbons or less and mixtures thereof. A preferred foamable liquid composition includes from 1 to 4 percent, by weight, lactic acid, from 1 to 50, preferably from 5 to 30 percent, by weight, of an alcohol having from one to four carbon atoms, such as methanol, ethanol, propanol and mixtures thereof, and one or more water soluble solvents, such as butylene glycol, glycerin, polyglycerin, ethylene glycol, and propylene glycol. Preferably, said alcohol is ethanol and preferably said water soluble solvent is propylene glycol in an amount of from 1 to 20 percent, by weight, and more preferably from 5 to 15 percent, by weight, of the foamable liquid composition.

The liquid foam composition according to the invention contains at least one surfactant. Preferably, the foamable liquid composition comprises from 0.1 to 5 percent, by weight, of a surfactant, more preferably from 0.2 to 1 percent, by weight of a surfactant. Suitable surfactants have emulsifying, solvating, and foam-forming or foam-stabilizing properties; are preferably nonionic; and have a hydrophilic-lipophilic balance (HLB) value of greater than about fifteen. In particular, the surfactant oleth-20 is preferred in an amount of from 0.1 to 5 percent, by weight, of the foamable liquid composition and more preferably from 0.2 to 1 percent, by weight, of the foamable liquid composition.

Other surfactants optionally used with the present formulation include, but are not limited to: any combination of anionic, cationic, non-ionic, or amphoteric surfactants with an HLB value of greater than fifteen.

Optionally, the foam formed is maintained with a foam stabilizer. In the treatment of the human scalp for androgenic alopecia the maintenance of foam is important to allow a known and suitable period of contact of the minoxidil and bimatoprost with the scalp.

The foam stabilizer is preferably included in the foamable liquid composition in an amount of from 0.05 to 0.5 percent, and more preferably from 0.1 to 0.5 percent, by weight. In particular, the stabilizer includes lauryl glucoside in an amount of from 0.05 and 0.5% by weight and more preferably from 0.1 to 0.5 percent, by weight, of the foamable liquid composition.

Other optional foam stabilizers used with the present liquid composition include, but are not limited to: fatty amine oxides, a quaternary amines, or a cellulose derivatives, such as methyl cellulose and ethyl cellulose.

The liquid composition can be sprayed on the scalp daily to stimulate the growth of hair.

EXAMPLE 12

A gel comprising bimatoprost and minoxidil in a pharmaceutically-acceptable solvent comprising propylene glycol and alcohol and a cross-linked acrylic polymer thickening agent such as a Carbomer, e.g. Carbomer 934P, is prepared as described below. The cross-linked acrylic polymer thickening agent is neutralized with a neutralizing agent such as diisopropanolamine The gel comprises from 0.0000001% to 10% bimatoprost and from 0.001% to 10% minoxidil, by weight. More preferably said gel comprises from 0.01% to 0.5% bimatoprost and from 1% to 5% minoxidil, by weight, most preferably said composition comprises 0.03% bimatoprost and 5% minoxidil, by weight.

Said pharmaceutically acceptable solvent is selected from the group consisting of ethanol, propanol, butanol, propylene glycol, dipropylene glycol, hexylene glycol, 1,3-butylene glycol, PEG-200, PEG-400, glycerol and mixtures thereof.

Most preferably, said solvent is selected from the group consisting of ethanol and isopropanol.

Alternatively, said solvent selected from the group consisting of propylene glycol, dipropylene glycol, hexylene glycol, 1,3-butylene glycol, PEG-200, PEG-400, and glycerol.

Most preferably, said solvent is propylene glycol.

In a second alternative embodiment of the invention, said solvent comprises a mixture comprising a first solvent selected from the group consisting of ethanol, propanol and butanol and a second solvent selected from the group consisting of propylene glycol, dipropylene glycol, hexylene glycol, 1,3-butylene glycol, PEG-200, PEG-400, and glycerol.

Preferably, in said second alternative embodiment of the invention, said solvent comprises a mixture of ethanol and propylene glycol.

The gel further comprising a neutralizing agent, wherein said neutralizing agent may be selected from the group consisting of ammonium hydroxide, arginine, 2-amino-2-methyl-1-propanol, dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, aminomethyl propanol, sodium hydroxide, and potassium hydroxide.

A pharmaceutically elegant gel comprising minoxidil and bimatoprost is prepared by mixing the below-described mixtures:

| Ingredient | % w/w |
|---|---|
| Part I | |
| Purified water USP | q.s. 100 |
| Carbopol ® 934P | 0.45 |
| Part II | |
| Bimatoprost | 0.03 |
| Minoxidil | 5 |
| propylene glycol USP | 10 |
| alcohol USP | 13 |
| diisopropanolamine NF | 0.45 |
| Part III | |
| alcohol USP | 27 |

The component parts are prepared separately. Part III is then mixed with Part I. When a uniform mixture is obtained, Part II is then added using planetary mixing under vacuum until a uniform gel is obtained.

What is claimed is:

1. A composition of bimatoprost and minoxidil in a vehicle for topical application to the skin of a mammal whereby the combination of bimatoprost and minoxidil produces a faster onset of hair growth as compared to compositions comprising bimatoprost and minoxidil, alone.

2. The composition of claim 1, wherein bimatoprost and minoxidil are administered as a composition comprising from 0.0000001% to 10% bimatoprost and from 0.001% to 10% minoxidil, by weight.

3. The composition of claim 2, wherein bimatoprost is present at a concentration from about 0.01% to about 5% by weight.

4. The composition of claim 3, wherein bimatoprost is present at a concentration of about 0.1% by weight.

5. The composition of claim 3, wherein bimatoprost is present at a concentration of about 1% by weight.

6. The composition of claim 3, wherein bimatoprost is present at a concentration of about 3% by weight.

7. The composition of claim 3, wherein bimatoprost is present at a concentration of about 5% by weight.

8. The composition of claim 1, wherein bimatoprost is provided as a pharmaceutically acceptable salt.

9. The composition of claim 2, wherein minoxidil is present at a concentration from about 0.5% to about 5% by weight.

10. The composition of claim 9, wherein minoxidil is present at a concentration of about 1% by weight.

11. The composition of claim 9, wherein minoxidil is present at a concentration of about 2% by weight.

12. The composition of claim 9, wherein minoxidil is present at a concentration of about 5% by weight.

13. The composition of claim 1, wherein the composition is adapted for topical application to mammalian skin as a foam, wherein said foam comprises bimatoprost, minoxidil, and at least one surfactant, wherein the surfactant optionally includes a foam stabilizer; an aqueous-alcohol solvent, and wherein said aqueous-alcohol solvent comprises water and an alcohol.

14. The composition of claim 1, wherein the composition is adapted for topical application to mammalian skin as a gel, wherein said gel comprises bimatoprost, minoxidil, and at least one surfactant.

15. The composition of claim 1, wherein the composition is adapted for topical application to mammalian skin as a topical ointment, wherein said topical ointment comprises bimatoprost, minoxidil, and is formulated using at least one of an oleaginous, water-soluble, and emulsion-type base.

16. The composition of claim 1, wherein the composition is adapted for topical application to mammalian skin as an aqueous solution.

17. The composition of claim 16, wherein the aqueous solution further comprises at least one viscosity-increasing agent.

18. The composition of claim 17, wherein the at least one viscosity-increasing agent is selected from the group consisting of polysaccharides, mucopolysaccharides, and polyalcohols.

19. The composition of claim 16, wherein the aqueous solution further comprises at least one additive selected from the group consisting of EDTA, sorbitol, and boric acid.

20. The composition of claim 1, wherein the composition is adapted for topical application to mammalian skin as an oil solution.

21. The composition of claim 1, wherein the composition further comprises at least one preservative.

22. The composition of claim 21, wherein the at least one preservative is selected from the group consisting of benzalkonium chloride, chlorhexidine, chlorobutanol, parahydroxybenzoic acids and phenylmercuric salts.

* * * * *

UNITED STATES PATENT AND TRADEMARK OFFICE
CERTIFICATE OF CORRECTION

PATENT NO. : 9,700,503 B2  
APPLICATION NO. : 14/561561  
DATED : July 11, 2017  
INVENTOR(S) : David F. Woodward et al.

Page 1 of 1

It is certified that error appears in the above-identified patent and that said Letters Patent is hereby corrected as shown below:

On the Title Page

In item (54), in Column 1, delete "COMPOSITION" and insert -- METHOD --, therefor.

Signed and Sealed this  
Fifth Day of September, 2017

Joseph Matal  
*Performing the Functions and Duties of the*  
*Under Secretary of Commerce for Intellectual Property and*  
*Director of the United States Patent and Trademark Office*